(12) United States Patent
Fujii et al.

(10) Patent No.: US 7,336,810 B2
(45) Date of Patent: Feb. 26, 2008

(54) SKIN EVALUATION METHOD AND IMAGE SIMULATION METHOD

(75) Inventors: Makoto Fujii, Kita-ku (JP); Emina Horikoshi, Kita-ku (JP); Takao Someya, Kita-ku (JP); Yuko Misaki, Kita-ku (JP); Ichiro Sasaki, Kita-ku (JP)

(73) Assignee: Kosé Corporation, Tokyo (JP)

( * ) Notice: Subject to any disclaimer, the term of this patent is extended or adjusted under 35 U.S.C. 154(b) by 235 days.

(21) Appl. No.: 10/560,136

(22) PCT Filed: Dec. 10, 2003

(86) PCT No.: PCT/JP03/15775

§ 371 (c)(1),
(2), (4) Date: Dec. 9, 2005

(87) PCT Pub. No.: WO2004/110264

PCT Pub. Date: Dec. 23, 2004

(65) Prior Publication Data

US 2007/0092160 A1   Apr. 26, 2007

(30) Foreign Application Priority Data

Jun. 11, 2003   (JP)   ............................ 2003-167040
Jun. 12, 2003   (JP)   ............................ 2003-167957

(51) Int. Cl.
   *G06K 9/00*   (2006.01)
(52) U.S. Cl. .................... 382/128; 382/286; 382/108; 356/600; 356/369; 356/445; 600/476; 600/407
(58) Field of Classification Search ................ 382/128, 382/286, 108; 356/600, 369, 445; 600/476, 600/407
See application file for complete search history.

(56) References Cited

U.S. PATENT DOCUMENTS 5,557,324 A * 9/1996 Wolff ........................ 345/207

5,870,491 A * 2/1999 Kawai et al. ............... 382/181

(Continued)

FOREIGN PATENT DOCUMENTS

JP   5-220130   8/1993

(Continued)

OTHER PUBLICATIONS

Liquid Crystal Polarization Camera, Wolff et al., Apr. 1997.*

(Continued)

*Primary Examiner*—Samir Ahmed
*Assistant Examiner*—Nancy Bitar
(74) *Attorney, Agent, or Firm*—Oblon, Spivak, McClelland, Maier & Neustadt, P.C.

(57) ABSTRACT

A skin beauty evaluation method for imaging an object such as human face to obtain digital image data, extracting data on a mirror reflection light component of each pixel from the digital image data and evaluating the skin sheen and skin beauty by using this. A simulation image obtaining method is also disclosed.

By using these methods, it is possible to objectively evaluate the skin sheen and beauty which have been conventionally evaluated only subjectively. Thus, the methods are useful for development of a new skin cosmetic material.

Moreover, by using a polarized light source, a digital camera to which polarization filter can be attached and a computer having a predetermined calculation or analysis equation, it is possible to easily evaluate the customer skin sheen and beauty and perform simulation of the face state of a test subject after improvement of the skin state or makeup. Accordingly, the methods are also hopeful for promoting sale of cosmetics at the cosmetic counter of a department store, or at a cosmetic store or a drug store.

3 Claims, 13 Drawing Sheets

U.S. PATENT DOCUMENTS

| | | | |
|---|---|---|---|
| 6,400,996 B1* | 6/2002 | Hoffberg et al. | 700/83 |
| 6,624,890 B2* | 9/2003 | Backman et al. | 356/369 |
| 6,640,145 B2* | 10/2003 | Hoffberg et al. | 700/83 |
| 6,804,003 B1* | 10/2004 | Wang et al. | 356/369 |
| 7,127,280 B2* | 10/2006 | Dauga | 600/407 |
| 7,200,281 B2* | 4/2007 | Zhang et al. | 382/276 |

FOREIGN PATENT DOCUMENTS

| | | |
|---|---|---|
| JP | 7-75629 | 3/1995 |
| JP | 07-231883 | 9/1995 |
| JP | 2002-078683 | 3/2002 |
| JP | 2004-166801 | 6/2004 |

OTHER PUBLICATIONS

Fujii, Makoto, et al., "Taju Kaizodo Kaiseki o Mochiita, Hada no Tsuya no Kyakkanteki Hyoka Hoho no Kaihatsu", Dai 51 Kai SCCJ Kenkyu Toronkai Koen Yoshishu, The Society of Cosmetic Chemists of Japan, pp. 13 to 16, 2002. (with English abstract).

Ojima, Nobutoshi et al., The Appearance of Skin with Make-up (II) (Analysis on Surface Topography of Skin with Make-up), Graduate School of Science and Technology, Society of Photographic Science and Technolgy of Japan, vol. 56, No. 4, pp. 264 to 269, 1993. (with English abstract).

* cited by examiner

SKIN EVALUATION METHOD AND IMAGE SIMULATION METHOD

TECHNICAL FIELD

The present invention relates to a skin evaluation method using image analysis, and in particular a skin evaluation method capable of objectively evaluating the luster and beauty of a skin and a simulation method capable of obtaining a variety of simulation images having different textures by using image analysis from two digital images picked up under specific conditions.

BACKGROUND ART

A beautiful skin is a great desire to every woman. In order to maintain the healthy condition of a skin as well as make the skin more beautiful and maintain a rich luster, basic cosmetics and makeup cosmetics are widely used.

It is requested to evaluate, by some method, how beautiful a skin has turned or how lustrous a skin looks by maintaining the healthy condition of a skin or using appropriate cosmetics. In particular, there is an earnest request for a method to readily evaluate the degree of beauty or luster of the skin of a test subject at a cosmetics counter in a department store, a drugstore or a cosmetics store.

Beauty of a skin has been evaluated by visually performing a sensory evaluation, for example, by way of paired comparison. In this approach, a target of comparison is mandatory. It has been difficult to represent the beauty of a skin by way of some physical means in the absence of a control for comparison.

The luster of a skin surface is a key element for representing the health, beauty, or post-makeup finish of the skin. Thus, it is one of the key purposes of a basic cosmetic and a makeup cosmetic to provide a skin with a proper luster.

In order to develop a cosmetic having such effects, it is necessary to objectively measure the gloss of a skin that corresponds to the luster of a skin.

The gloss of a skin, influenced by the properties of a skin as a substance as well as sebum, a makeup film or the shape of a skin surface, is sometimes judged as "facial shine" that gives bad impression. It is thus less objective to evaluate the luster of a skin by way of a first-dimensional value alone such as the glossiness.

A prior art method is known for judging and evaluating the "facial shine" or "appearance of sebum". The method picks up the image of a skin with the skin surface under high contrast to obtain image data, distinguishes bright pixels that exceed a predetermined threshold and dark pixels that is below the threshold to obtain the number of bright pixels and the percentage of the area occupied by the bright pixels (refer to JP-A-3236731).

This method solely measures the glossiness of a skin, with the result varying with the way the threshold value is determined, so that it is hardly capable of evaluating the luster or beauty of a skin from an objective point of view.

Further, the health, beauty or post-makeup finish of a skin of a face or the like is a major concern to many women. A woman may wish to know the details of how the overall appearance of her skin would change by improving the health of her skin, such as skin problems or by using a cosmetic. The answer is not given until the health of her skin is improved or the cosmetic is actually used.

Unlike this approach, a casual method is used for showing the appearance obtained in case the health of a skin is improved or the appearance obtained in case a cosmetic is used by using a photograph of an actual model. However, with the method, only the changes in appearance of the model can be observed, and not the user him/herself.

In view of the foregoing circumstances, it has been requested to provide an evaluation method capable of objectively measuring the luster or beauty of a skin and giving an evaluation similar to the one by an observation with naked eyes.

Further, it has been requested to provide a method for simulating changes in the appearance of a target such as a human face by simply changing the roughness of a texture or the like of the target at a cosmetics counter in a department store, a drugstore or a cosmetics store.

DISCLOSURE OF THE INVENTION

The inventors have earnestly made examinations in order to solve the above problems and have noticed that the favorable gloss of a skin is determined by a physical glossiness and the texture of a skin. The inventors have found that it is possible to obtain the "apparent roughness" representing the glossiness and texture from a single digital color image by way of image analysis and thereby objectively indicating the luster of a skin in the course of accomplishing the invention.

The inventors have also found that among the components included in an image picked up under a certain polarized lighting, a mirror-reflected light component showing the shapes and the texture, in particular, high-frequency components showing minute surface shapes (texture) has a dispersion value that is highly correlated with the result of a sensory evaluation visually performed on the beauty of a skin. By using this correlation, the beauty of a skin can be objectively evaluated without a control for comparison.

Further, the inventors have also found that an internally reflected light component indicating an appearance color component and a mirror-reflected light component indicating the shapes and the texture can be separated from an image digitally picked up under a polarized lighting and an image digitally picked up under the polarized lighting through a filter having a plane of polarization orthogonal to the polarized lighting. Further, they found that by applying various operations such as multiresolution analysis to the images, re-synthesizing the images, and synthesizing the resulting image with an internally reflected light component, a simulation image can be obtained with only the texture of a target being changed and the colors and shape of the images being unchanged.

A first object of the invention is to provide a method comprising the steps:

(A1) imaging the skin of a test subject and obtaining digital image data;

(A2) extracting the data of mirror-reflected light components of respective pixels from the digital image data;

(A3) obtaining the average value of the brightness of the respective pixels from the data of the mirror-reflected light components and defining the result as physical glossiness;

(A4) applying multiresolution analysis to the data of the mirror-reflected light components to separate the data into respective data of a plurality of different frequency components, selecting data of a plurality of middle-frequency components representing the texture of a skin from the data, synthesizing the selected data and defining the synthesized data as reconstructed image data, squaring the data of the respective pixel components of the reconstructed image data, obtaining the average value and defining the result as an apparent roughness of a skin surface; and (A5) representing the luster state of the skin by the physical glossiness and the apparent roughness of the skin surface.

A second object of the invention is to provide a method comprising:

(B1) imaging a target skin under a polarized lighting and obtaining digital image data;

(B2) imaging the same target skin under the polarized lighting by using a polarizing filter having a plane of polarization orthogonal to the plane of polarization of the polarized lighting and obtaining digital image data;

(B3) extracting data of a mirror-reflected light component from the digital image data obtained in steps (B1) and (B2);

(B4) performing multiresolution analysis on the data of the mirror-reflected light component extracted in step (B3), separating the data into data of a plurality of different frequency components, and selecting data of a plurality of high frequency components;

(B5) synthesizing the selected high frequency components and defining the synthesized data as reconstructed image data;

(B6) determining the dispersion of respective pixel components of the reconstructed image data; and (B7) associating an average value of the dispersion values obtained in step (B6) with the beauty of the skin.

A third object of the invention is to provide a method comprising:

(C1) imaging a target under a polarized lighting and obtaining digital image data;

(C2) imaging the same target under the polarized lighting by using a polarizing filter having a plane of polarization orthogonal to the plane of polarization of the polarized lighting and obtaining digital image data;

(C3) extracting data of a mirror-reflected light component and data of an internally reflected light component from the digital image data obtained in steps (C1) and (C2);

(C4) performing multiresolution analysis on the data of the mirror-reflected light component extracted in step (C3) and separating the data into data of a plurality of different frequency components;

(C5) changing the data of a desired frequency component among the respective data of the separated plurality of different frequency components;

(C6) synthesizing the data of the frequency component that is changed with the data of the frequency components that are unchanged and defining the synthesized data as reconstructed image data; and (C7) synthesizing the reconstructed image data obtained in step (C6) with the internally reflected light component data obtained in step (C3) and obtaining a simulation image of the target.

BEST MODE FOR CARRYING OUT THE INVENTION

Figure 1:
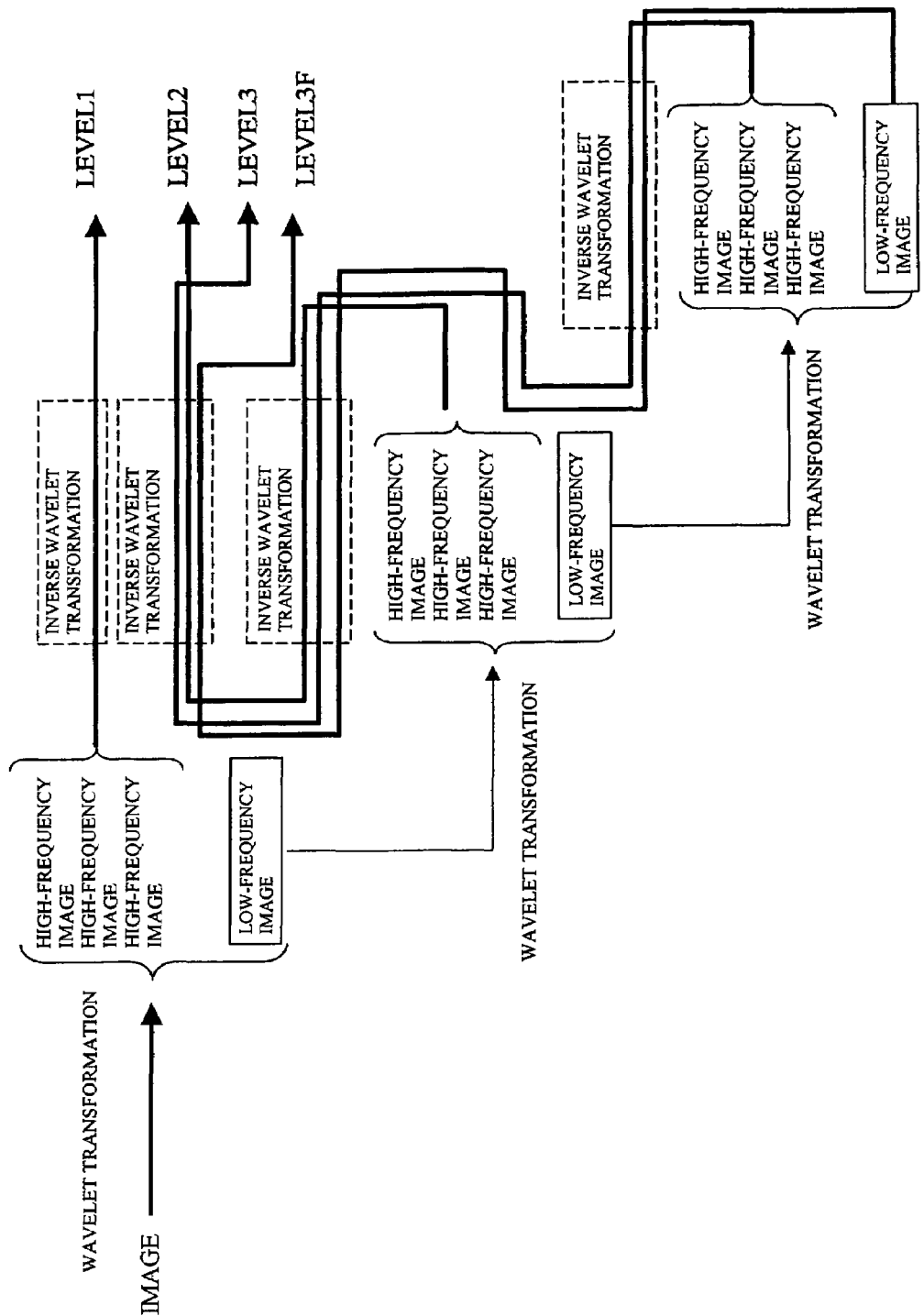
FIG. 1 shows the procedure of wavelet transformation and inverse wavelet transformation.

In order to implement the inventive method, it is necessary to pick up an image of a test subject and obtain digital image data.

The image pickup process is performed using a general digital camera. The number of pixels of a digital camera is not particularly limited as long as it is possible to obtain digital image data in the form of RGB values or the like.

A method for evaluating the luster of a skin including steps (A1) through (A5) according to the invention (hereinafter referred to as the first aspect) is implemented in accordance with the following principle.

First, the digital image data obtained by using a digital camera or the like includes a mirror-reflected light component and an internally reflected light component. In general, the color of mirror-reflected light is the same as that of the light source while the color of internally reflected light is one specific to an object. This phenomenon is called the dichromatic reflection model. The invention uses the model to extract data of a mirror-reflected light component of each pixel from digital image data.

According to the dichromatic reflection model, the measurement value i(R,G,B) of each pixel as pixel data of a digital image can be represented as shown in Expression (1) by using a skin color unit vector $k_B$(Br,Bg,Bb) and a light source color unit vector $k_S$(Sr,Sg,Sb). In the expression, $i_S$ represents the intensity of mirror-reflected light and $i_B$ the intensity of internally reflected light.

$$i = i_S k_S + i_B k_B = (i_S \quad i_B) \begin{pmatrix} k_S \\ k_B \end{pmatrix} \quad (1)$$

By using a matrix to represent all measurement values of image data, Expression (2) is obtained:

$$I = I_{SB} K_{SB} \quad (2)$$

I is a matrix of n by 3. $I_{SB}$ is a matrix of n by 2. $K_{SB}$ is a matrix of 2 by 3. Since $K_{SB}$ is not a square matrix, $I_{SB}$ is not uniquely determined. Thus, the Moor-Penrose generalized inverse matrix $K_{SB}^+$ is used to assume a reflected light intensity matrix $I_{SB}$ by using Expression (3).

$$I_{SB} = IK_{SB}^+ \qquad (3)$$

By doing so, it is possible to obtain data of mirror-reflected light component of respective pixels. An average value of the brightness of each pixel of the mirror-reflected light component data is obtained and the average value is defined as physical glossiness as a first element of skin luster evaluation.

Next, the mirror-reflected light component data thus obtained is subjected to multiresolution analysis and separated into a plurality of different frequency components and respective data is obtained.

The respective data of the separated mirror-reflected light components includes influences of surface shapes such as the skeleton of face, flesh, pores and wrinkles and sebum distributed on a skin surface. In other words, the data of a mirror-reflected light component is a synthesis of varying components of various scales. Components derived from minute shapes on the skin surface such as pores and wrinkles that may have various influences on the texture of the skin are separated from the varying components.

Separation of these varying components is performed by multiresolution analysis that decomposes image data to a linear coupling of another image and examines the characteristics of the original image data. To be more specific, the data of a mirror-reflected light component as image data is subjected to two-dimensional fast wavelet transformation to be decomposed into an approximate image obtained by approximation using a lower-frequency function and an error image of a high-frequency component that is an error with respect to the original image. The approximate image is further decomposed by way of wavelet transformation so as to obtain images representing high-frequency components from the low-frequency component of the original image. By synthesizing the images decomposed into high-frequency components from a low-frequency component as appropriate, it is possible to reconstruct the original image. Decomposition and reconstruction of the image may be made using, for example, second- to tenth-order (N=2-10) Daubechies wavelet transformation.

The procedure of the wavelet transformation and inverse wavelet transformation is shown in FIG. 1 at a simplified level for ease of description.

Three items of high-frequency image data and one item of low-frequency data are obtained from the original image data by way of wavelet transformation. The three items of high-frequency image data are subjected to inverse wavelet transformation and the resulting data is defined as level 1 image data (data of a highest frequency). Then, the low-frequency image obtained above is subjected to wavelet transformation again to obtain three high-frequency images and one low-frequency image anew. The three high-frequency images are subjected to inverse wavelet transformation twice and the resulting data is defined as level 2 image data (data of a second-highest frequency). The above low-frequency image is subjected to wavelet transformation and the three high-frequency images obtained are subjected to inverse wavelet transformation three times. The resulting data is defined as level 3 image data (data of a third-highest frequency). While FIG. 1 depicts no further details, it is possible to obtain a plurality of image data from low frequencies to high frequencies by repeating the above procedure. On the other hand, the low-frequency image data obtained as a result of the third wavelet transformation is subjected to inverse wavelet transformation three times. The resulting data is defined as level 3F image data. The wavelet transformation and the inverse wavelet transformation can be easily made based on a method described for example in a reference document "Weburetto henkan no kiso to Ouyou mathematics de manabu" (Basis and application of Wavelet transform learning with mathematica), Yoshifuru Saito, Asakura shoten.

Among the above data, image data of a plurality of middle-frequency components assumed to reflect pores and wrinkles is extracted and these data is synthesized and the resulting data is defined as reconstructed image data. The data of each pixel component is squared and an average value is obtained and is defined as the apparent roughness that is a second element of skin luster evaluation.

Based on the physical glossiness and the apparent roughness of a skin thus obtained, the luster state of the skin is represented. Various representation methods are available. For example, plotting on an XY plane, or substituting the numerical value into an equation for calculation of, for example, a glossiness index of a skin, etc. is given.

As a specific approach as an evaluation method for the luster of a skin that is based on the above principle, the steps of the first aspect, that is, the following steps (A1) through (A5) are necessary:

(A1) imaging the skin of a test subject and obtaining digital image data;

(A2) extracting the data of mirror-reflected light components of respective pixels from the digital image data;

(A3) obtaining the average value of the brightness of the respective pixels from the data of the mirror-reflected light components and defining it as physical glossiness;

(A4) applying multiresolution analysis to the data of the mirror-reflected light components to separate the data into data of each of a plurality of different frequency components, selecting data of a plurality of middle-frequency components representing the texture of a skin from the data, synthesizing the data and defining the synthesized data as reconstructed image data, squaring the data of the respective pixel components of the reconstructed image data, obtaining the average value and defining it as an apparent roughness of a skin surface; and (A5) representing the luster state of the skin by the physical glossiness and the apparent roughness of the skin surface.

The method for evaluating the beauty of a skin including the steps (B1) through (B7) (hereinafter referred to as the second aspect) is described below.

To implement the second aspect, it is necessary to image a target under polarized lighting and obtain digital image data. This imaging process is performed twice on the same target, once by using a polarizing filter having a plane of polarization orthogonal to the plane of polarization of the polarized lighting (hereinafter referred to as the polarizing filter) and once without using the polarizing filter.

A unit used for the imaging process is mentioned earlier.

Of the digital data obtained, the digital image data obtained without using a polarizing filter in step (B1) includes a mirror-reflected light component and an internally reflected light component. On the other hand, the digital image data obtained using a polarizing filter in step (B2) includes an internally reflected light component alone. Of these components, the color of mirror-reflected light is the same as that of the light source while the color of internally reflected light is one specific to an object. This phenomenon is called the dichromatic reflection model. The invention uses the model to separate mirror-reflected light component data and internally reflected light component data of each pixel from the two types of digital image data.

First, a value of a digital image I picked up under polarized lighting S in coordinates x, y is defined as I(x,y). A value of a digital image $I_P$ picked up under polarized lighting S by using a polarizing filter P in coordinates x, y is defined as $I_P(x,y)$. According to the dichromatic reflection model, the measurement value I(x,y) of each pixel, which is pixel data of a digital image, is represented by Expression (4) by using an internally reflected light unit vector $k_B(x,y)$ and the irradiated light unit vector $k_S$. In the expression, $i_S(x,y)$ is the intensity of the mirror-reflected light and $i_B(x,y)$ is the intensity of the internally reflected light.

$$I(x,y) = i_S(x,y)k_S + i_B(x,y)k_B(x,y) \quad (4)$$

$I_P(x,y)$ is represented by Expression (5). However, a polarizing filter orthogonal to the polarized irradiation is used so that $i_s$ equals zero and thus $I_P(x,y)$ is represented by Expression (6).

$$I_P(x, y) = i_S(x, y)k_S + i_{BP}(x, y)k_{BP}(x, y) \quad (5)$$
$$= i_{BP}(x, y)k_{BP}(x, y) \quad (6)$$

Further, $k_{BP}(x,y)$ is a unit vector so that it is obtained by the following Expression (7):

$$k_{BP}(x, y) = I_P(x, y) / i_{BP} \quad (7)$$
$$= I_P(x, y) / |I_P(x, y)|$$

where $k_{BP}(x,y)$ is an internally reflected light vector assumed when the polarizing filter p is used. When $k_B(x,y)$ is approximated to be $k_{BP}(x,y)$, the following expression holds true.

$$I(x, y) = i_S(x, y)k_S + i_B(x, y)k_B(x, y) \quad (8)$$
$$= i_S(x, y)k_S + i_B(x, y)k_{BP}(x, y)$$
$$= [i_S(x, y) i_B(x, y)][k_S k_{BP}(x, y)]$$

When Expression (8) is represented by a matrix expression using the following matrix $I_{SB}(x,y)$ and $K(x,y)$ the following expression holds true.

$I(x,y) = I_{SB}(x,y) K(x,y)$

When the reflected light intensity matrix $I_{SB}(x,y)$ is estimated by using the Moor-Penrose generalized inverse matrix $K(x,y)^+$, the following expression holds true.

$$I_{SB}(x,y) = I(x,y) K(x,y)^+ \quad (9)$$

From Expression (9), $i_S(x,y)$ and $i_B(x,y)$ are obtained, so that the mirror-reflected intensity and the internally reflected light intensity are obtained as follows.

The mirror-reflected light intensity $i_S(x,y)$ is obtained by the following equation:

$i_S(x,y) = i_S(x,y) k_S$

The internally reflected light intensity $i_B(x,y)$ is obtained by the following equation:

$i_B(x,y) = i_B(x,y) k_{BP}$

Based on the above principle, it is possible to separate data of a mirror-reflected light component of each pixel from the digital images in steps (B1) and (B2). These steps are generally executed by loading the digital image I and the digital image $I_B$ into a computer and processing the images in accordance with the above expressions.

Next, the data of the mirror-reflected light component obtained in step (B3) is separated into respective data of a plurality of different frequency components by multiresolution analysis.

The separated data of the mirror-reflected light component includes both a component representing a shape and a component representing a texture so that it is separated into low-frequency components representing the overall three-dimensional effect (shape) of a target skin and high-frequency components representing the minute shapes (texture) of the surface of the target skin. To be more specific, for example, considering a face, the mirror-reflected light component includes surface shapes such as the skeleton of face, flesh, pores and wrinkles and sebum distributed on a skin. As a result, the mirror-reflected light component is separated into appropriate number of components among image components representing the three-dimensional effect of the entire face such as features (low-frequency components) and image components representing minute shapes of the skin surface such as pores (high-frequency components).

Separation of these varying components is performed by multiresolution analysis that decomposes the mirror-reflected light component data into linear coupling of another image and examines the characteristics of the original image data. To be more specific, the data of a mirror-reflected light component as image data is subjected to two-dimensional fast wavelet transformation to be decomposed into an approximate image obtained by approximation using a lower-frequency function and an error image of a high-frequency component that is an error with respect to the original image. The approximate image is further decomposed by way of wavelet transformation so as to obtain images representing high-frequency components from the low-frequency component of the original image. By synthesizing the images decomposed into high-frequency components from low-frequency component as appropriate, it is possible to reconstruct the original image. Decomposition and reconstruction of the image may be performed using, for example, second- to tenth-order (N=2-10) Daubechies wavelet transformation.

The procedure of wavelet transformation and inverse wavelet transformation is as described with respect to the first aspect of the invention.

From the data of the plurality of different frequency components thus separated, data of a plurality of high-frequency components related to the beauty of a skin is selected. For example, in the case where the mirror-reflected light component is separated into eight components, the third or fourth-highest frequency component is appropriately selected as an area where surface shapes such as pores and winkles may be reconstructed.

The high-frequency components thus selected may be synthesized to form reconstructed image data. Next, the dispersion values of all pixels of the reconstructed image data are calculated. The dispersion values may be obtained using a known method.

When the obtained dispersion values are averaged, the average value is substituted into a relation between an experimentally pre-acquired rank of the beauty of a skin and the average dispersion value in order to evaluate the beauty of the skin of a test subject.

An image simulation method (hereinafter referred to as the third aspect) including the steps (C1) through (C7) is described below.

To implement the third aspect, same as the second aspect, it is necessary to image a target under polarized lighting and obtain digital image data. This imaging process and a unit used are same as the second aspect of the invention.

The imaging process is performed twice on the same target, once by using a polarizing filter having a plane of polarization orthogonal to the plane of polarization of the polarized lighting (hereinafter referred to as the polarizing filter) and once without using the polarizing filter.

Of the digital data obtained, the digital image data obtained without using a polarizing filter in step (C1) includes a mirror-reflected light component and an internally reflected light component. On the other hand, the digital image data obtained using a polarizing filter in step (2) includes an internally reflected light component alone. Of these components, the color of mirror-reflected light is the same as that of the light source while the color of internally reflected light is one specific to an object. This phenomenon is called the dichromatic reflection model. The invention uses the model to separate mirror-reflected light component data and internally reflected light component data of each pixel from the two types of digital image data.

The principle of separating the mirror-reflected light component of each pixel (reflected light intensity; $I_S(x,y)$) and the internal reflected light component of each pixel (internal reflected light intensity; $I_B(x,y)$) is the same as that described in the second aspect of the invention.

Based on the above principle, it is possible to separate data of a mirror-reflected light component of each pixel from the digital images in steps (C1) and (C2). These steps are generally executed by loading the digital image I and the digital image $I_B$ into a computer and processing the images in accordance with the above expressions.

Next, the data of the mirror-reflected light component obtained in step (C3) is separated into a plurality of different frequency components by multiresolution analysis and respective data is obtained.

The separating method for separating the data of the mirror-reflected light component into an appropriate number of components, from low-frequency components representing the overall three-dimensional effect (shape) of a target (such as a skin) and high-frequency components representing the minute shapes (texture) of the surface of the target and the method for appropriately synthesizing high-frequency components from the separated low-frequency component and to reconstruct an image are the same as those described in the second aspect.

A characteristic of the third aspect of the invention is that some of the data of a plurality of frequency components separated as mentioned above is subjected to data change operation in accordance with a purpose of simulation in order to change the image like in step (C5). The data change operation includes emphasizing the frequency component through multiplication by a certain numeral and softening the frequency component through division by a certain numeral. When such operations are made on a plurality of frequency data items, the same operation or different operations may be used. In such an operation, multiplying high-frequency component data by a certain numeral emphasizes the texture while dividing the same by a certain numeral eventually obtains a soft appearance.

The data of a frequency component subjected to change operation in step (C5) is synthesized with a frequency component not subjected to change operation and reconstructed image data is obtained. The reconstructed image data is an image composed of a mirror-reflected light component of the target that has been partially modified. For example, in the case where a frequency component obtained by dividing high-frequency component data is used, the shapes such as the features are the same as those of an image composed of a mirror-reflected light component although the former provides a soft image with pebbling on the skin surface suppressed.

The reconstructed image data thus obtained is further synthesized with the digital image data (internally reflected light component) obtained in step (C3) so as to provide a simulation image including color information. The simulation image has some of its frequency components of the original digital image changed, so that the frequency components are either emphasized or softened.

For example, it is possible to obtain a simulation image with skin problems corrected or a post-makeup simulation image by softening high-frequency components from an image of an actual skin and synthesizing the resulting image with the original low-frequency component and internally reflected light components.

The percentage of softening the high-frequency components may be determined based on the test result of the improvement of actual skin problems and makeup effect. It is thus possible to obtain a simulation image with an extremely high accuracy.

Operation

The first aspect of the invention is characteristic in that the concept of "apparent roughness of a skin surface" is introduced as a value to represent a texture on top of glossiness for evaluating the luster of a skin.

Thus, according to the first aspect, it is possible to discriminate a case where "facial shine" or "appearance of sebum" is present from a case where a skin has a favorable natural luster, even though these cases are determined the same when the gloss of a skin is measured.

The second aspect of the invention is characteristic in that mirror-reflected light components included in two types of picked-up images are extracted and high-frequency components of the mirror-reflected light components are selected and that an average value of dispersion of data obtained by synthesizing these components is calculated in order to evaluate the beauty of the skin of a test subject.

According to the second aspect of the Invention, no subjective elements are included in the process from imaging to evaluation. This ensures objective evaluation of the beauty of a skin.

The third aspect of the invention is characteristic in that components included in two types of picked-up images are separated and emphasized or softened. Thus, various simulation images can be readily obtained.

EXAMPLES

The invention is detailed below by way of examples thereof. Note that the invention is not limited to these examples by any means.

Example 1

Figure 2:
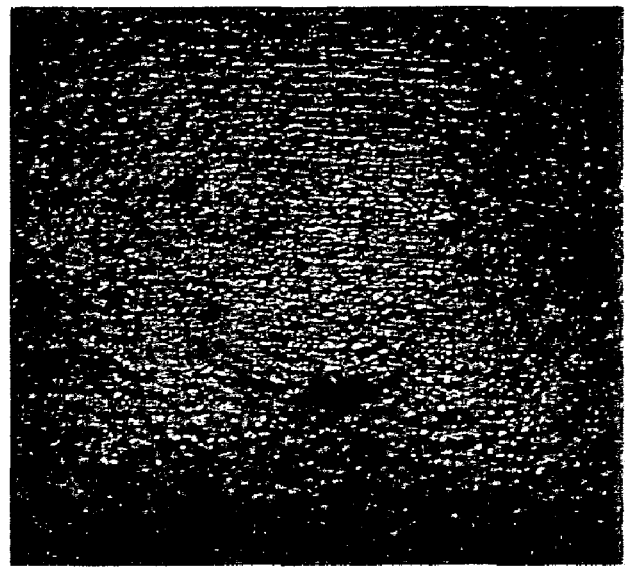
FIG. 2 shows a photograph of an example of a sample image used for analysis.

Calculation of the Physical Glossiness of a Skin and the Apparent Roughness of a Skin Surface:

The application state of foundation on the forehead of the same person was varied, and six samples with different glossiness were prepared. The samples were imaged with a digital camera under artificial sunshine and sample image data (512 by 512 pixels, 24-bit full color) for analysis was prepared. One of the sample images used for analysis is shown in FIG. 2.

Figure 3:
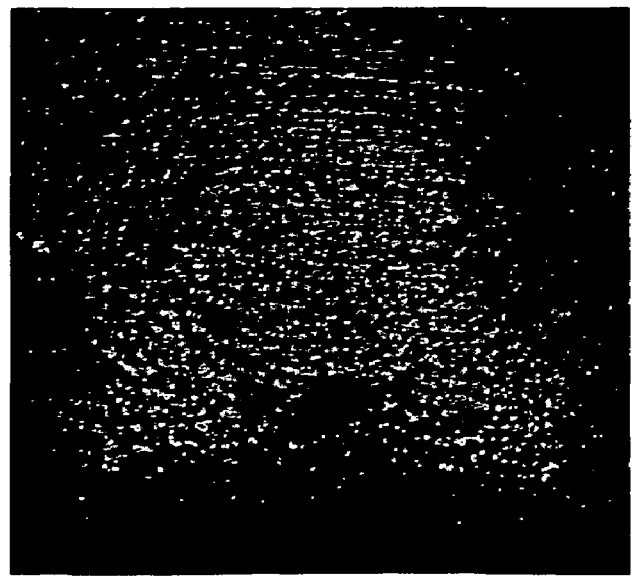
FIG. 3 shows a photograph of image data of the intensity of mirror-reflected light obtained from a sample image.

For these images, a reflected light intensity matrix $I_{SB}$ was obtained using the measurement value i(R,G,B) of each pixel and a measured light source color unit vector $k_S$(Sr, Sg,Sb) by way of the Moor-Penrose generalized inverse matrix $K_{SB}^+$. The mirror-reflected light intensity of each pixel was sequentially obtained and an average value of the brightness was defined as a physical glossiness. FIG. 3 shows an image of the data of the mirror-reflected light intensity obtained from FIG. 2. The image in FIG. 3 emphasizes shades that represent the shapes of the skin surface. It is understood that the texture information is not lost even after the analysis.

Figure 4:
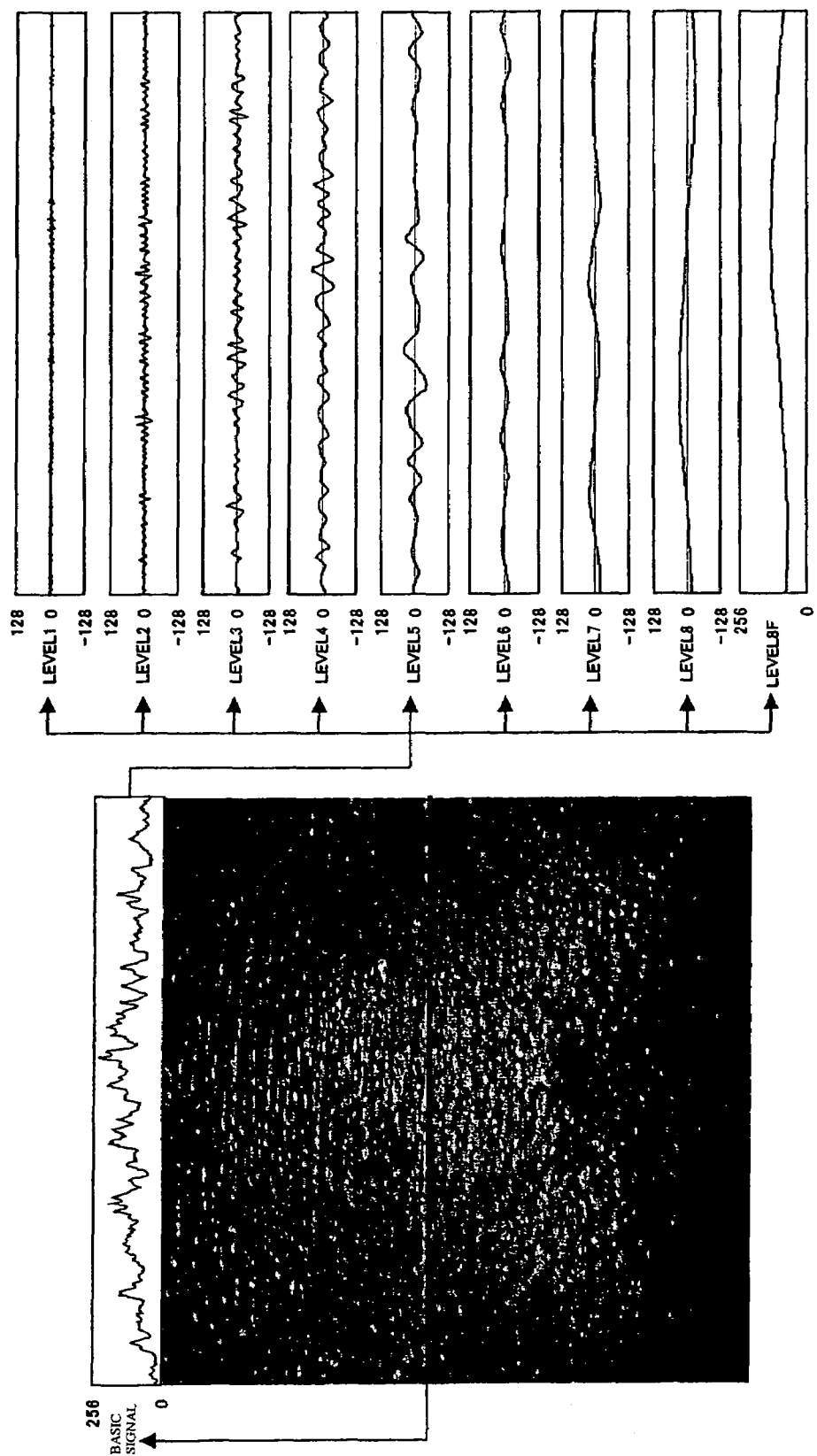
FIG. 4 shows the result of multiresolution analysis on changes in the brightness in the image along a straight line.
Figure 5:
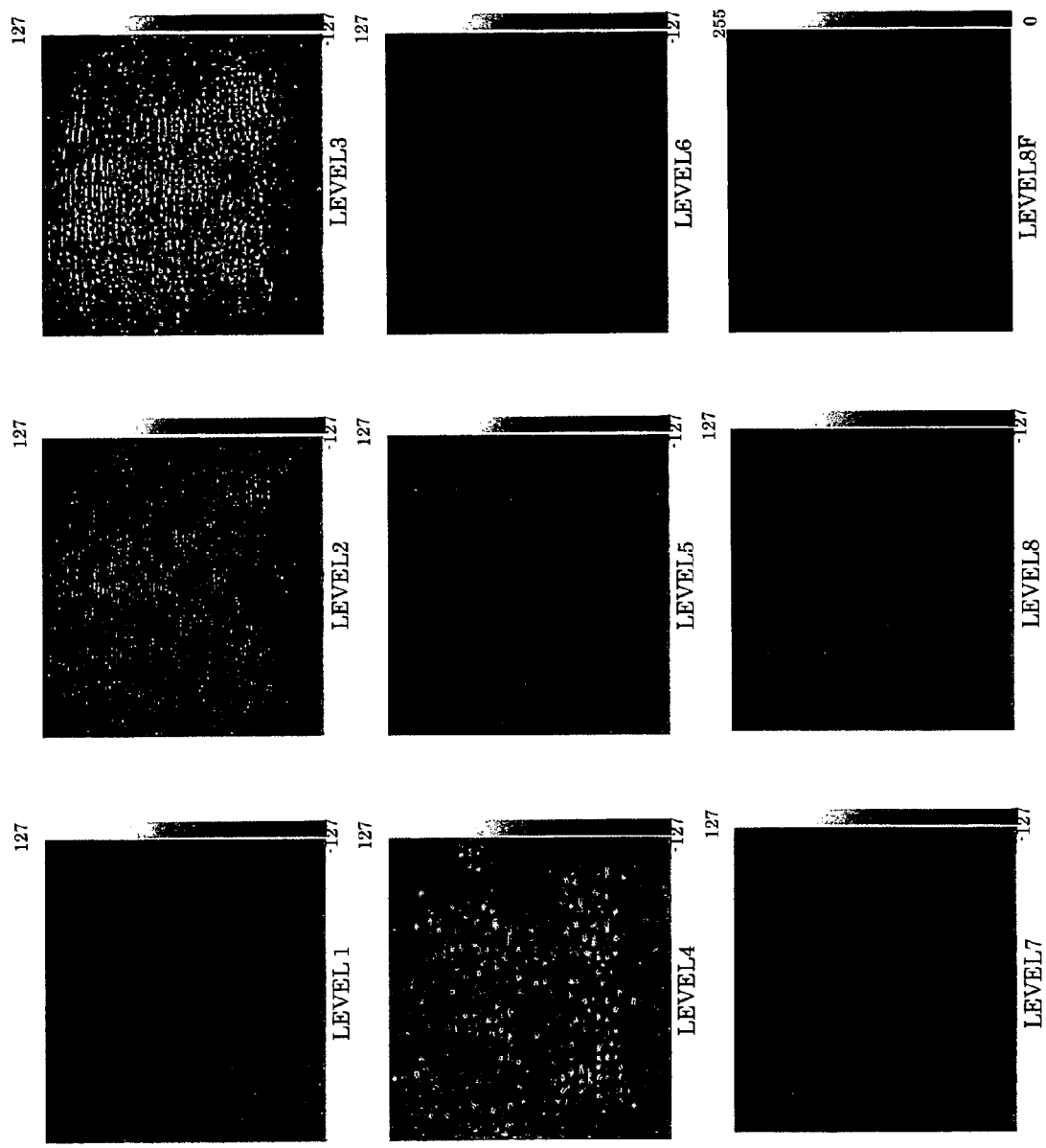
FIG. 5 shows a photograph of image data of the result of multiresolution analysis on the data of the intensity of mirror-reflected light.

From the data of the mirror-reflected light intensity, multiresolution analysis was performed using wavelet transformation and inverse wavelet transformation in order to separate components that represent a texture. In the procedure of wavelet transformation and inverse wavelet transformation, the image size was 256 by 256 pixels and the fourth-order (N=4) Daubechies wavelet transformation was used. FIG. 4 shows the result of multiresolution analysis on changes in the brightness along a straight line in the image. FIG. 5 shows images of mirror-reflected light intensity data subjected to multiresolution analysis up to level 8. Level 8F is an approximate image obtained by approximating the image in FIG. 3 with a low-frequency function. Images at levels 1 to 8 are error images to represent error components between the approximate image and the mirror-reflected light image in FIG. 2. Level 1 represents an error image of the highest-frequency component. As the level increases, the corresponding frequency becomes lower. By totalizing the images at all levels, it is possible to reconstruct the mirror-reflected light image in FIG. 3.

Figure 6:
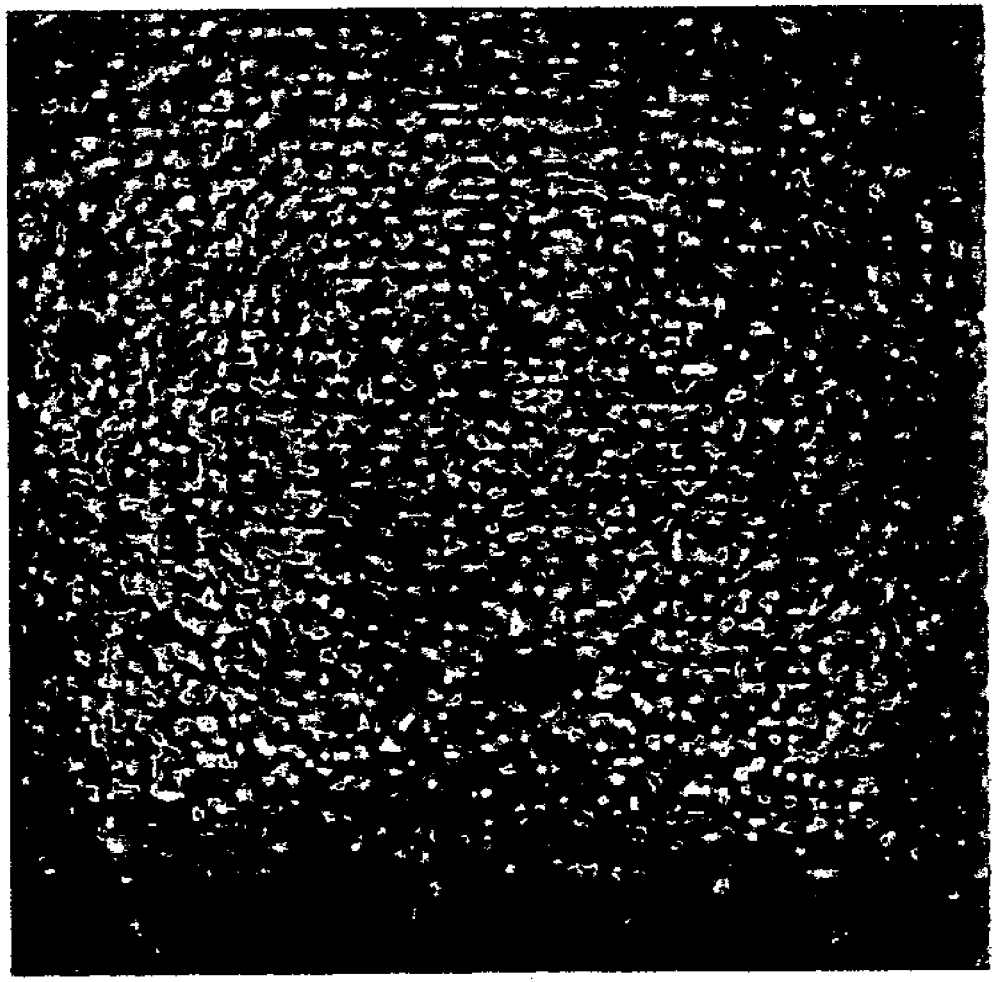
FIG. 6 is a photograph of an image of reconstructed data.

Middle-frequency components at levels 3 through 6 that best represent the characteristics of the shades of a skin surface were synthesized to form reconstructed data based on FIG. 5. An image of the reconstructed data is shown in FIG. 6. The image is a characteristic separation of minute shades of the skin surface from the mirror-reflected light image in FIG. 3. The shades of the components of this image are emphasized when the skin surface is rough or apparently looks rough due to the influence of makeup film or sebum. The data of each pixel component of the reconstructed data was squared and an average value is obtained. The value was defined as "apparent roughness" used as an index to represent a texture.

Example 2

Correlation between the apparent roughness of a skin surface and a psychological glossiness by sensory evaluation:

Six sample images used in Example 1 were evaluated by six panel members and the psychological glossiness of each member was converted into a number by way of Nakaya's variation (paired comparison). Marks A, B, C, D, E and F were given in descending order of psychological glossiness.

Figure 7:
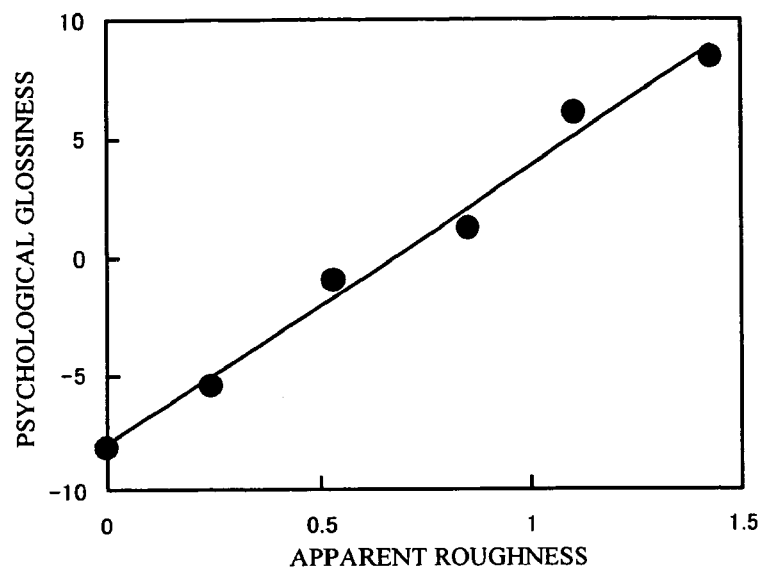
FIG. 7 shows correlation between the apparent roughness of a skin surface and a psychological glossiness obtained by sensory evaluation.

The numbers and the values of "apparent roughness" obtained in Example 1 were plotted as shown in FIG. 7, showing that these numbers were highly correlative.

From this, it is understood that the value of "apparent roughness" obtained in Example 1 may be used to reflect a psychological glossiness.

Example 3

Evaluation of Luster of Skin:
Concerning six sample images used in Example 1, the "physical glossiness" and "apparent roughness" were plotted using the sample image F that gained the lowest mark of psychological glossiness as shown in FIG. 8.

Figure 8:
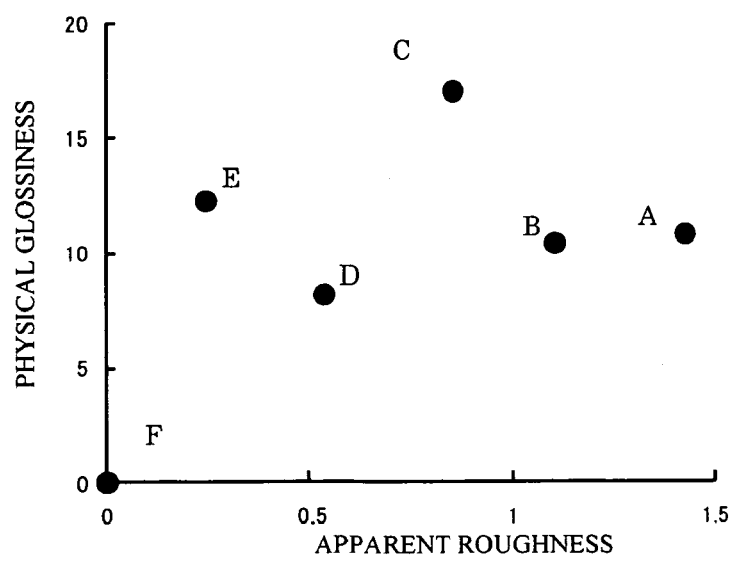
FIG. 8 is a representation of the luster of a skin by using a physical glossiness and an apparent roughness.

In FIG. 8, the "physical glossiness" indicates the amount of gloss and the "apparent roughness" indicates the quality of gloss thus it is possible to grasp the relative relation of gloss between images. For example, in FIG. 8, the horizontal axis represents the quality of gloss while the vertical axis represents the amount of gloss. After grasping the current luster state of a skin referring to FIG. 8, selecting foundation that will lead the skin to a favorable luster state will improve the makeup effect.

Example 4

Image Sampling Method:
Under polarized lighting perpendicular to a reflection plane, the entire surface of a human face was imaged by using a digital camera to obtain image data (512 by 512 pixels, 24-bit full color).

Under the same polarized lighting, the entire surface of the human face was imaged through a filter having a plane of polarization orthogonal to the plane of polarization of the polarized lighting by using the same digital camera to obtain polarized image data (512 by 512 pixels, 24-bit full color).

Figure 9:
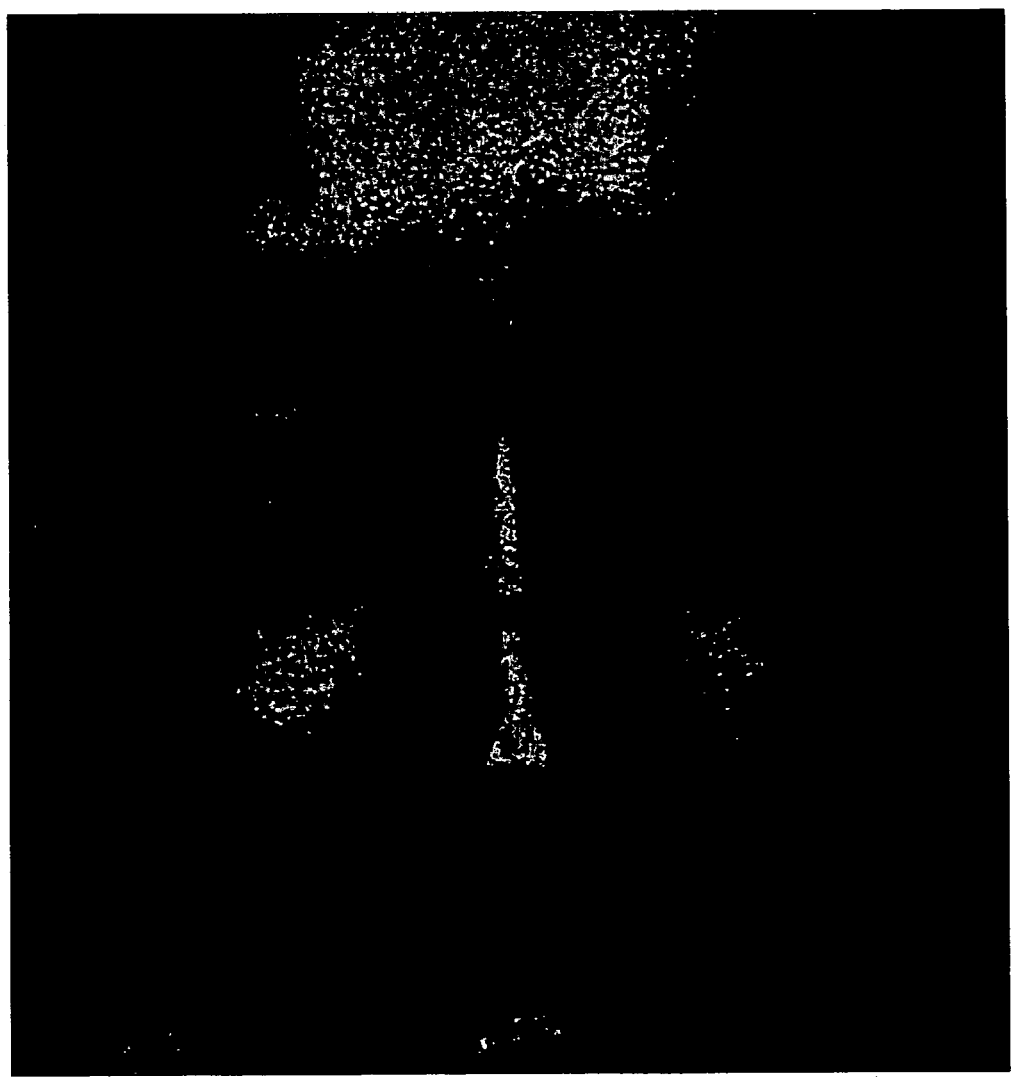
FIG. 9 shows a photograph of a sample image reconstructed solely by a mirror-reflected light component.

For these images, the measurement value I(x,y) of each pixel of image data and the measurement value $I_P$(x,y) of each pixel of polarized image data were obtained based on the dichromatic reflection model. A reflected light intensity matrix $I_{SB}$(x,y) was obtained from I(x,y) and $I_P$(x,y) by using a measured light source unit vector $k_S$ and a unit vector $k_B$(x,y) of each pixel of polarized image data by way of the Moor-Penrose generalized inverse matrix K(x,y)$^+$. FIG. 9 shows an image reconstructed by a mirror-reflected light component alone from the reflected light intensity matrix. In FIG. 9, x and y are the coordinates of the image I. The image in FIG. 9 emphasizes shades that represent the shapes of the face. It is understood that the texture information is not lost.

Figure 10:
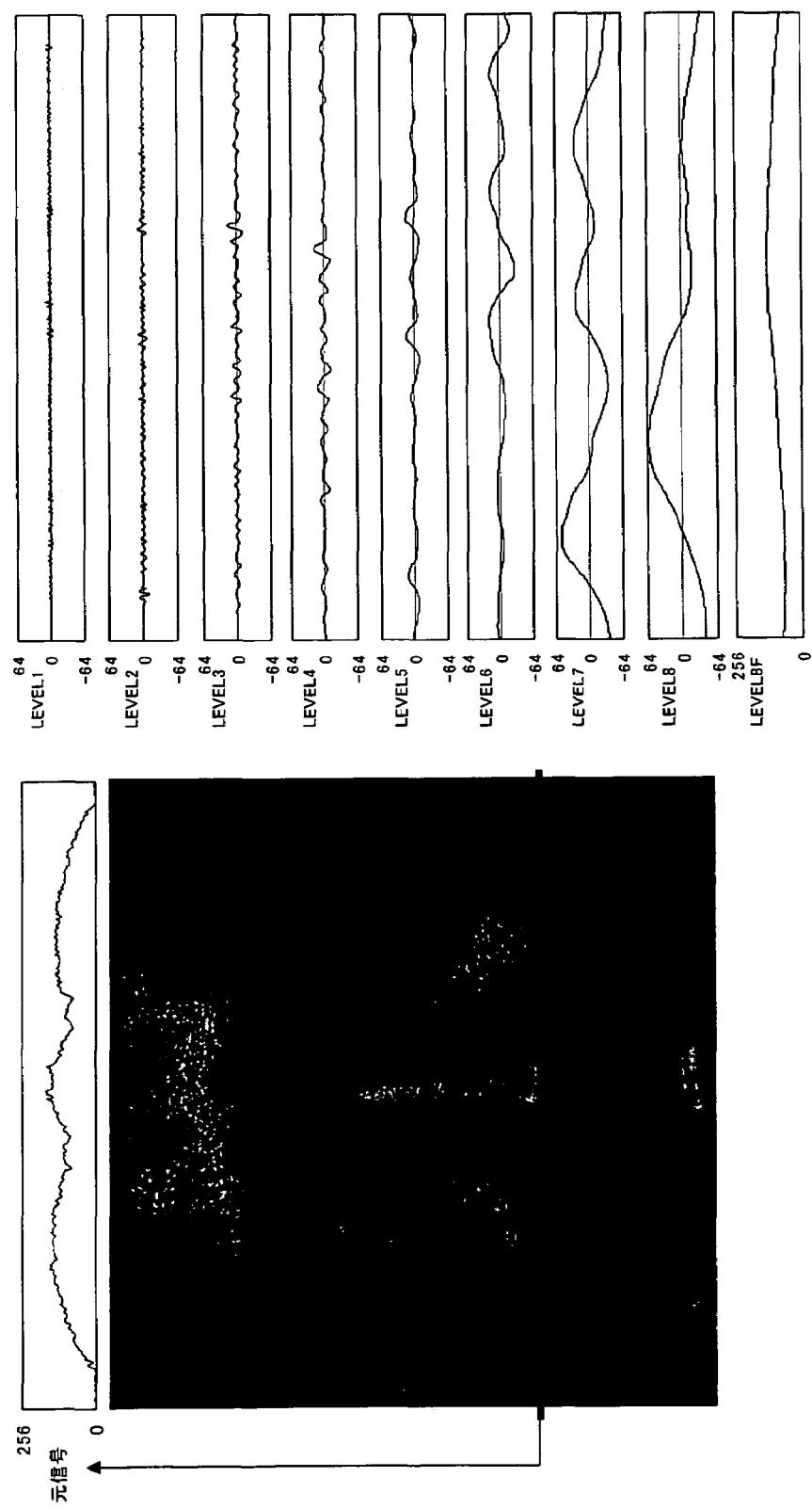
FIG. 10 shows the result of multiresolution analysis on changes in the brightness in the sample image along a straight line.
Figure 11:
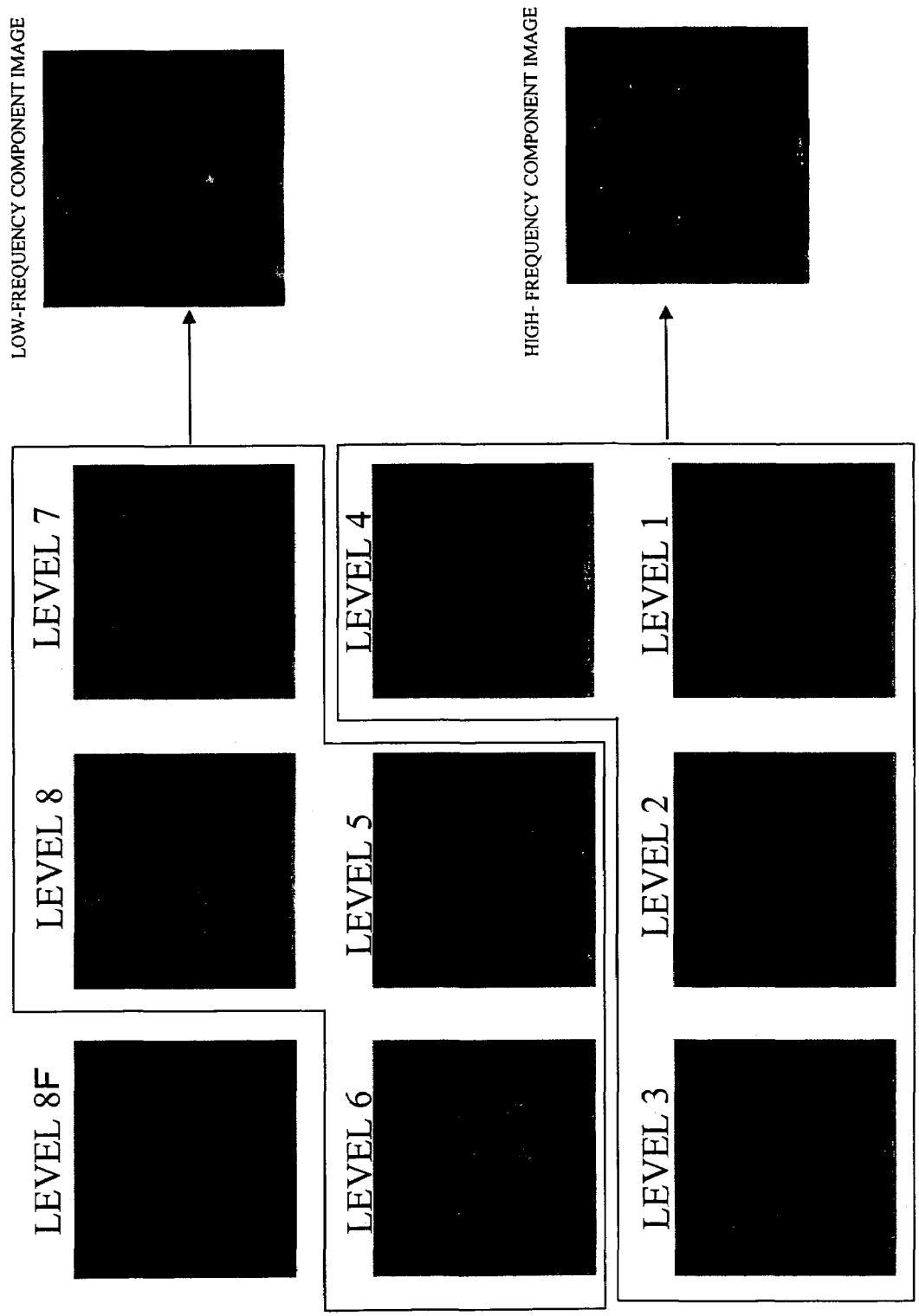
FIG. 11 shows a photograph of mirror-reflected light data separated into eight data items by multiresolution analysis.

Multiresolution analysis was performed by repeating wavelet transformation and inverse wavelet transformation from the mirror-reflected light intensity data. In the above procedure of wavelet transformation and inverse wavelet transformation, the image size was 512 by 512 pixels and the fourth-order (N=4) Daubechies wavelet transformation was used. FIG. 10 shows the result of multiresolution analysis on changes in the brightness in the image along a straight line. FIG. 11 shows an image of mirror-reflected light data subjected to multiresolution analysis up to level 8. Level 8F is an approximate image obtained by approximating the image in FIG. 2 with a function of the lowest frequency. Images at levels 1 to 8 are error images to represent error components between the approximate image and the mirror-reflected light image in FIG. 9. Level 1 represents an error image of the highest-frequency component. As the level increases, the corresponding frequency becomes lower. By totalizing the images at all levels, it is possible to reconstruct the mirror-reflected light image in FIG. 9.

Based on FIG. 11, only high-frequency components at levels 1 through 4 that best represent the characteristics of the shades of a skin surface were synthesized to form reconstructed data. The data of each pixel component of the reconstructed data was squared and an average value was obtained. The value was defined as an "average dispersion value".

Example 5

Figure 12:
FIG. 12 shows a photograph of the faces of panel members according to Example 5.
Figure 12:
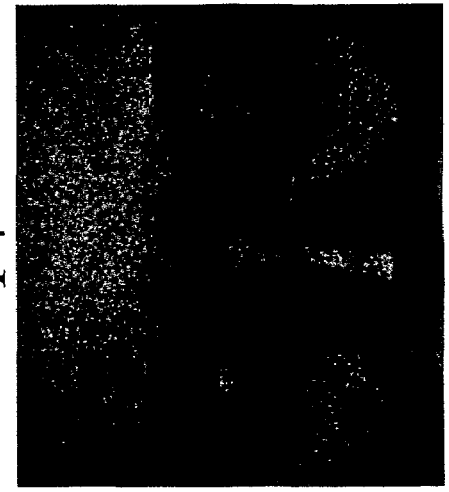
Figure 12:
Figure 12:
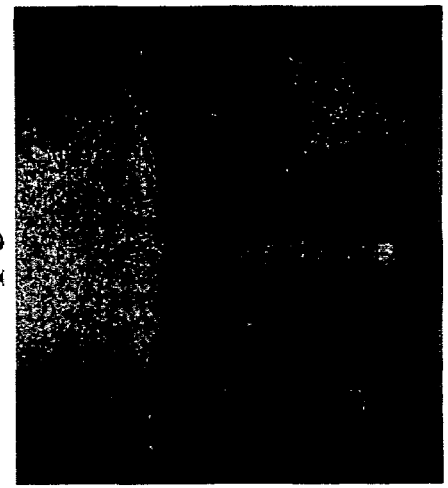
Figure 12:
Figure 12:
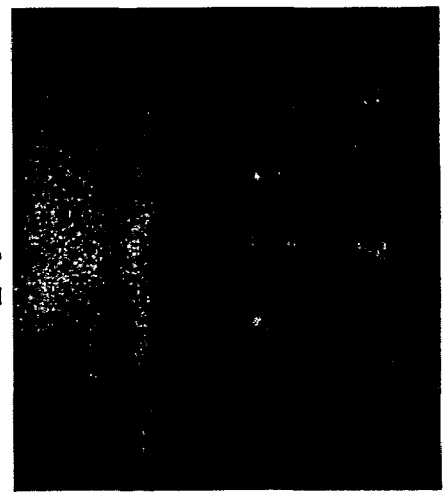

Correlation Between an "Average Dispersion Value" and the Beauty of Skin:
The face without makeup of each of the six panel members (males and females in twenties and thirties, P1-P6) as shown in FIG. 12 was digitally imaged in accordance with the method described in Example, 1 and subjected to calculation using the method in Example 4 in order to obtain the "average dispersion value" of each member.

Figure 13:
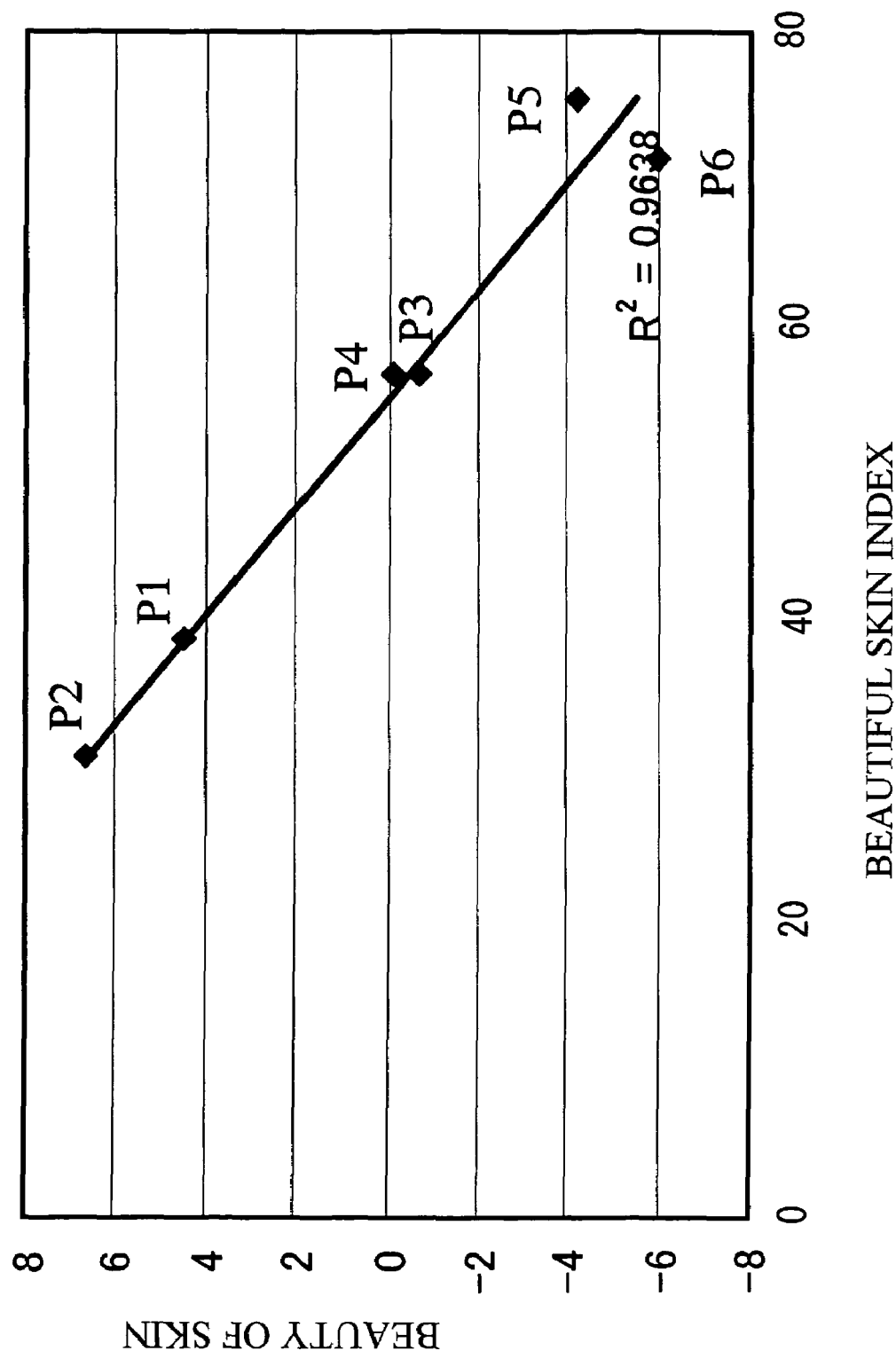
FIG. 13 shows the correlation between the "average dispersion value" according to Example 5 and the beauty of a skin.

The images of the six panel members (FIG. 12) were subjected to Nakaya's variation (paired comparison) by nine raters to convert the beauty of skin to a number. The numbers representing the "beauty of skin" and the values of "average dispersion" obtained were plotted. The result showed that these numbers were highly correlative (FIG. 13).

From this, it is understood that the "average dispersion value" obtained in Example 4 may be used to reflect the beauty of a skin. By calculating the average dispersion value, it is possible to grasp the relative beauty of a skin without preparing a control.

Example 6

Image Simulation Method:

Same as Example 4, the entire surface of a human face was imaged twice, under polarized lighting, once by using a filter having a plane of polarization orthogonal to the plane of polarization of the polarized lighting and once without using the filter.

For these images, same as Example 4, the measurement value I(x,y) of each pixel of image data and the measurement value $I_P(x,y)$ of each pixel of polarized image data were obtained based on the dichromatic reflection model. A reflected light intensity matrix $I_{SB}(X,Y)$ was obtained from I(x,y) and $I_P(x,y)$ by using a measured light source unit vector $k_S$ and a unit vector $k_B(x,y)$ of each pixel of polarized image data by way of the Moor-Penrose generalized inverse matrix $K(x,y)^+$. A corresponding figure shows, similar to FIG. 9 of Example 4, an image reconstructed by a mirror-reflected light component alone from the reflected light intensity matrix. It is understood that the image emphasizes shades representing the shades of the shapes and that the texture information is not lost.

Same as Example 4, multiresolution analysis was performed by repeating wavelet transformation and inverse wavelet transformation from the mirror-reflected light intensity data in order to separate components that represent a texture.

The result of multiresolution analysis on changes in the brightness in the image along a straight line by using the image of 512 by 512 pixels and the fourth-order (N=4) Daubechies wavelet transformation is the same as that shown in FIG. 10 of Example 4. An image of mirror-reflected light data subjected to multiresolution analysis up to level 8 is the same as that shown in FIG. 11 of Example 4. Level 8F is an approximate image obtained by approximating the image in FIG. 9 with a function of the lowest frequency. Images at levels 1 to 8 are error images to represent error components between the approximate image and the mirror-reflected light image in FIG. 9. Level 1 represents an error image of the highest-frequency component. As the level increases, the corresponding frequency becomes lower. By totalizing the images at all levels, it is possible to reconstruct the mirror-reflected light image in FIG. 9.

Figure 14:
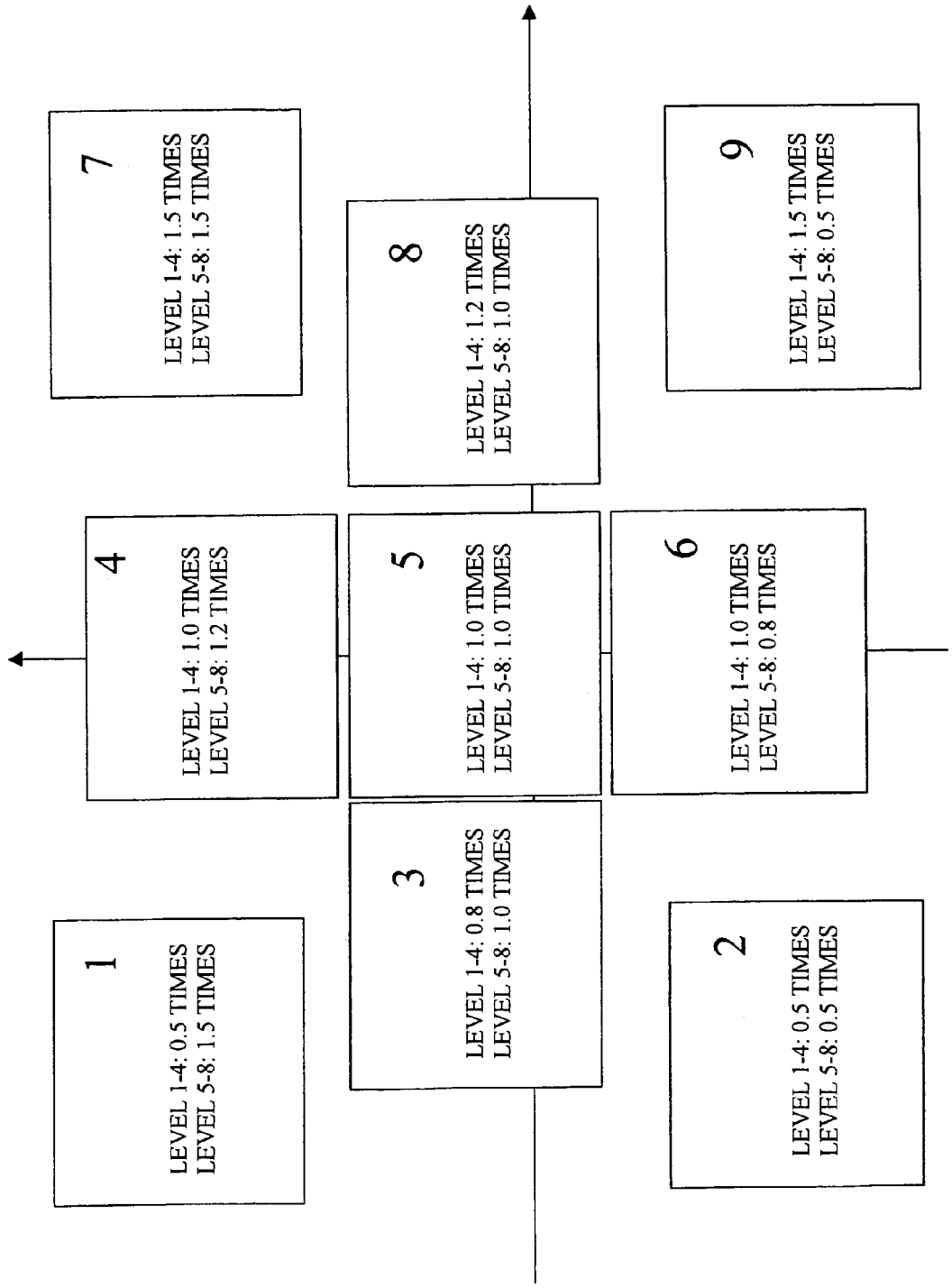
FIG. 14 shows a change operation to the mirror-reflected light data separated into eight data items.
Figure 15:
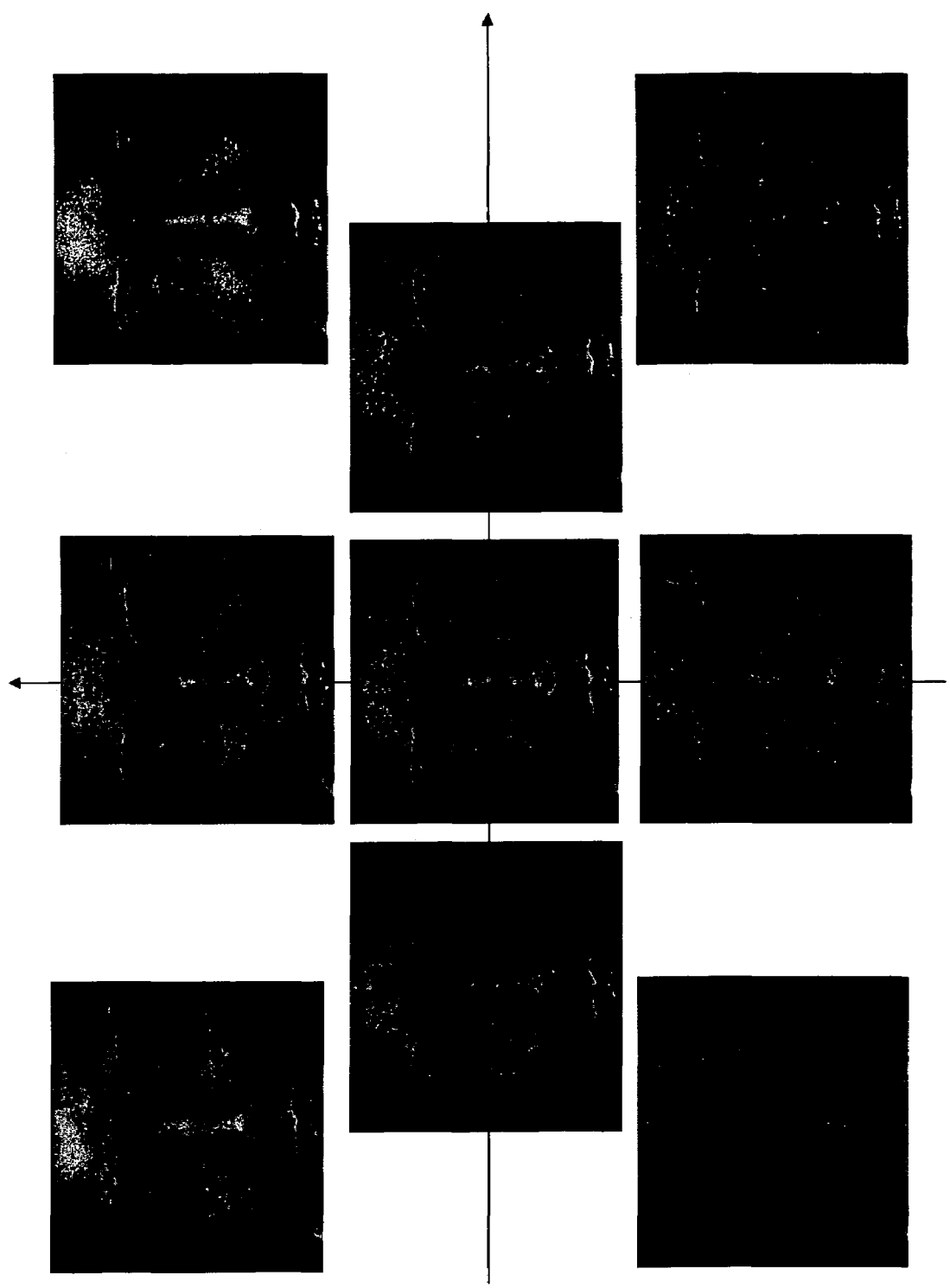
FIG. 15 shows a photograph of the images obtained by reconstructing the modified mirror-reflected light data and synthesizing the data with the internally reflected light component.

Based on FIG. 11, components of the image were separated into high-frequency components (levels 1 through 4) that best represent minute characteristics of the surface of a face such as pores and acne and low-frequency components (levels 5 through 8). These components were increased or decreased as shown in FIG. 14 and a mirror-reflected light image was reconstructed. An internally reflected light image was further added to prepare a simulation image (FIG. 15) having a different texture from that of the original digital image.

INDUSTRIAL APPLICABILITY

According to the first aspect of the invention, the luster of a skin evaluation of which has been ambiguous can be clearly represented with the amount and quality of gloss, which is useful in evaluating the efficacy of giving luster to the skin. Thus, the first aspect can be advantageously used, for example, in the development of new skin cosmetics.

According to the second aspect of the invention, the beauty of a skin evaluation of which has been ambiguous can be represented with a numeric value. The second aspect is useful in evaluating the beauty of a skin and can be advantageously used, for example, in the development of new skin cosmetics.

According to the third aspect of the invention, simulation images having different textures or the like can be readily obtained from a small number of picked-up images.

Further, the invention readily evaluates the luster or beauty of the skin of a customer as well as simulates the state of the skin of the test subject assumed after improvement of the skin state or the state of a face assumed after a makeup, by using a polarized light source, a digital camera or the like to which a polarizing filter is attachable, and a computer in which a predetermined calculation or analysis expression is incorporated. The invention is thus applicable to sales promotion at a cosmetics counter in a department store, a cosmetics store or a drugstore or the like.

The invention claimed is:

1. A method for evaluating the beauty of a skin, comprising:
   (B1) imaging a target skin under a polarized lighting and obtaining digital image data;
   (B2) imaging the same target skin under the polarized lighting by using a polarizing filter having a plane of polarization orthogonal to the plane of polarization of the polarized lighting and obtaining digital image data;
   (B3) extracting data of a mirror-reflected light component from the digital image data obtained in steps (B1) and (B2);
   (B4) performing multiresolution analysis on the data of the mirror-reflected light component extracted in step (B3), separating the data into data of a plurality of different frequency components, and selecting data of a plurality of high frequency components;
   (B5) synthesizing the selected high frequency components and defining the synthesized data as reconstructed image data;
   (B6) determining the dispersion of respective pixel components in terms of the reconstructed image data; and
   (B7) associating an average value from values of the dispersion obtained in step (B6) with the beauty of the skin.

2. The method for evaluating the beauty of a skin according to claim 1, wherein extraction of data of a mirror-reflected light component in step (B3) is made by using a dichromatic reflection model and a Moor-Penrose generalized inverse matrix.

3. The method for evaluating the beauty of a skin according to claim 1 or 2, wherein the multiresolution analysis in step (B4) is performed by repeating wavelet transformation and inverse wavelet transformation to separate a mirror-reflected light component into data of a plurality of different frequency components.

* * * * *